United States Patent
Wildeman

(10) Patent No.: US 6,869,660 B2
(45) Date of Patent: Mar. 22, 2005

(54) FASTENER FABRIC AND RELATED METHOD

(75) Inventor: Martin Wildeman, Spartanburg, SC (US)

(73) Assignee: Tictex International, Ltd., Spartanburg, SC (US)

( * ) Notice: Subject to any disclaimer, the term of this patent is extended or adjusted under 35 U.S.C. 154(b) by 186 days.

(21) Appl. No.: 10/212,333

(22) Filed: Aug. 5, 2002

(65) Prior Publication Data

US 2004/0022992 A1 Feb. 5, 2004

(51) Int. Cl.[7] .............................. B32B 3/02; D04H 11/08
(52) U.S. Cl. .............................. 428/92; 428/94; 428/95; 428/96; 428/99; 442/401
(58) Field of Search .............................. 428/92, 93, 94, 428/95, 96, 99; 442/401

(56) References Cited

U.S. PATENT DOCUMENTS

| | | | |
|---|---|---|---|
| 3,589,147 A | 6/1971 | Price, Jr. ......................... 68/5 |
| 4,035,881 A | 7/1977 | Zocher ......................... 28/111 |
| 4,042,453 A | 8/1977 | Conway et al. ............. 162/108 |
| 4,739,635 A | 4/1988 | Conley et al. ................. 66/190 |
| 4,770,917 A | 9/1988 | Tochacek et al. ............. 428/95 |
| 4,931,343 A | 6/1990 | Becker et al. ................. 428/95 |
| 5,119,643 A | 6/1992 | Conley et al. ................. 66/190 |
| 5,401,554 A | 3/1995 | Armen ......................... 428/96 |
| 5,462,766 A | 10/1995 | Markusch et al. .......... 427/244 |
| 5,654,066 A * | 8/1997 | Pacione ....................... 428/95 |
| 5,692,949 A * | 12/1997 | Sheffield et al. ............. 428/94 |
| 5,695,845 A | 12/1997 | Ogawa et al. ................ 428/93 |
| 5,725,927 A | 3/1998 | Zilg et al. ..................... 428/89 |
| 5,740,578 A | 4/1998 | Moore ....................... 15/147.2 |
| 6,428,526 B1 * | 8/2002 | Heindel et al. ............. 604/391 |
| 2002/0132084 A1 | 9/2002 | Fink et al. ..................... 428/85 |

* cited by examiner

Primary Examiner—Cheryl A. Juska
Assistant Examiner—Jenna-Leigh Befumo
(74) Attorney, Agent, or Firm—J. M. Robertson; Intellectual Prop, LLC

(57) ABSTRACT

A multi-layer sheet material for use as a portion of a tear away fastening system. The sheet material includes a substrate layer and loop forming yarns extending through the substrate layer such that the loop forming yarns define an arrangement of loop elements projecting away from one side of the substrate layer. The loop elements are interconnected by portions of the yarns disposed across the other side of the substrate layer. A backing layer is disposed in overlying relation to the substrate layer to hold the loop forming yarns in place.

22 Claims, 9 Drawing Sheets

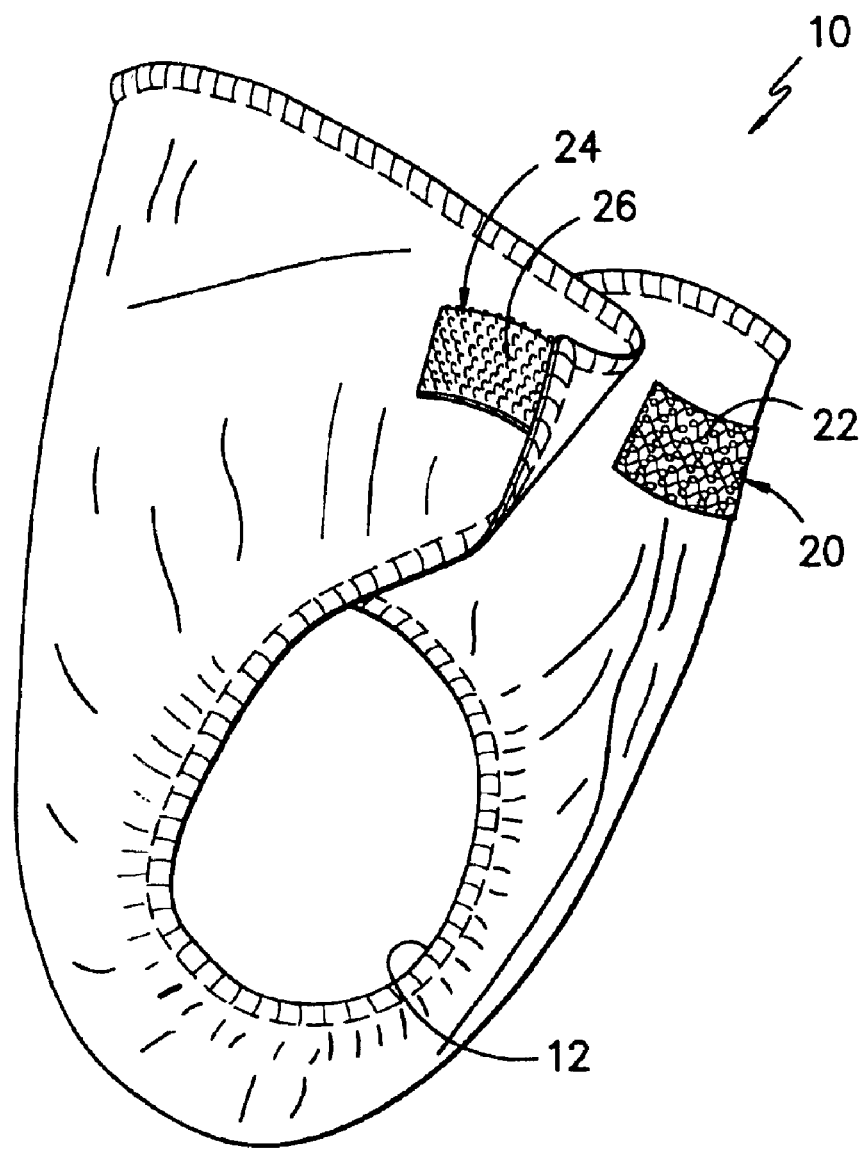
FIG. -1-

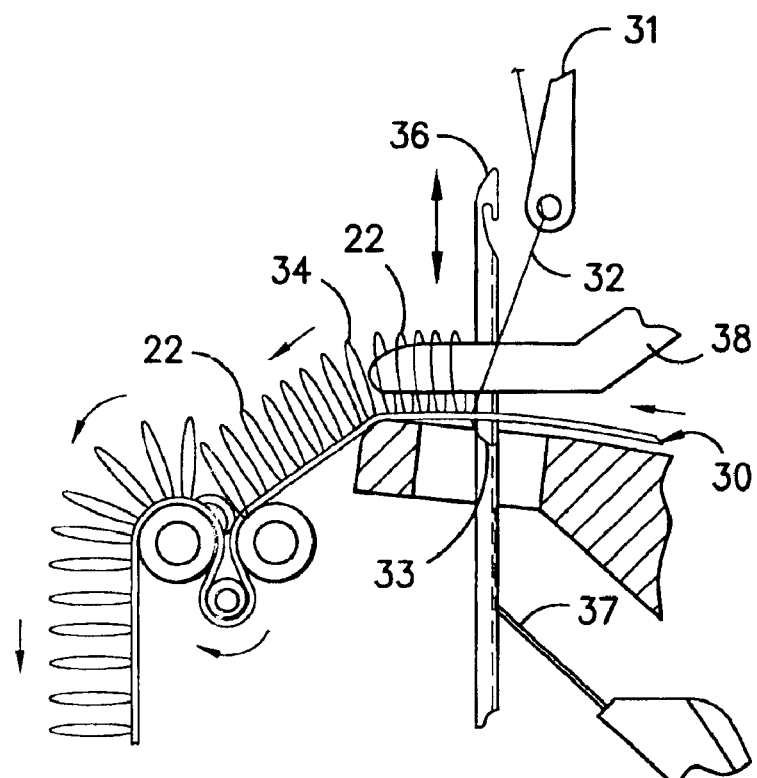
FIG. -2-
PRIOR ART
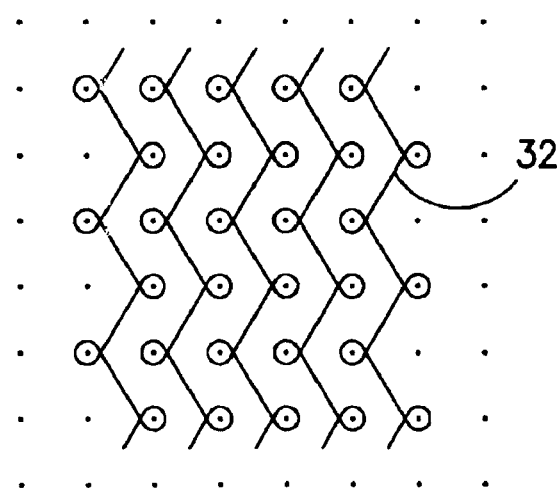
FIG. -3-
PRIOR ART

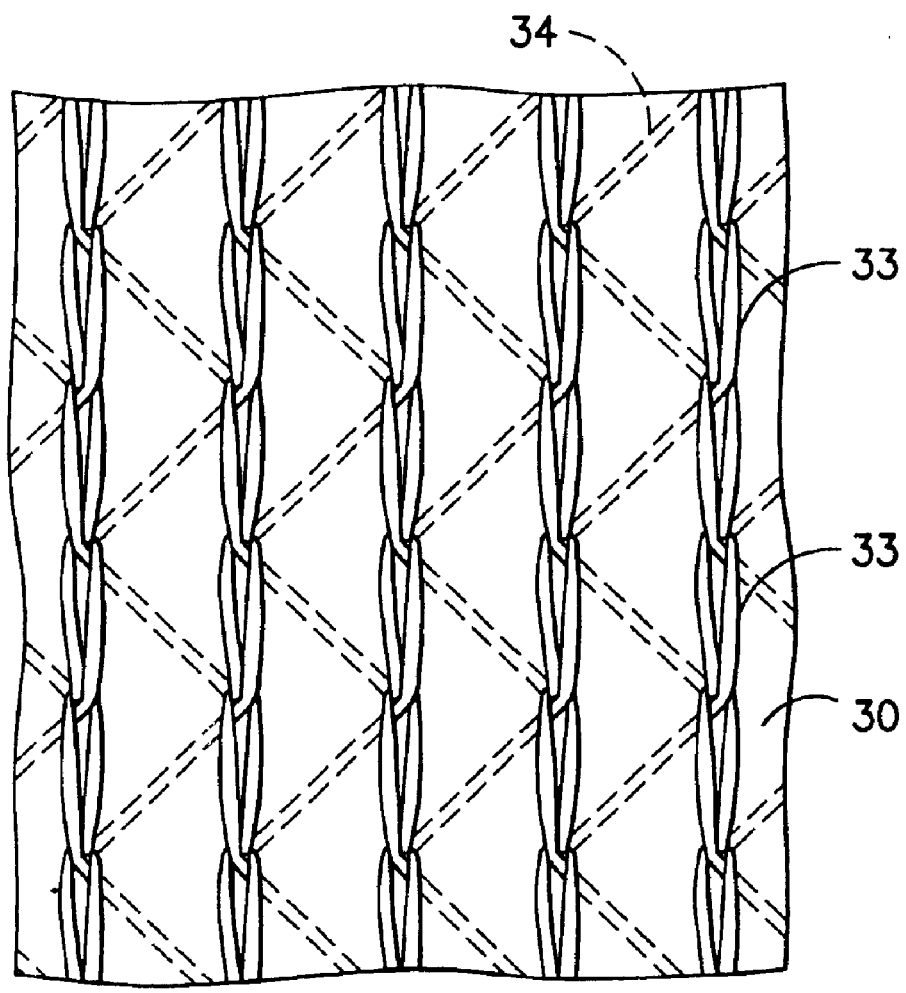
FIG. —3A—
PRIOR ART

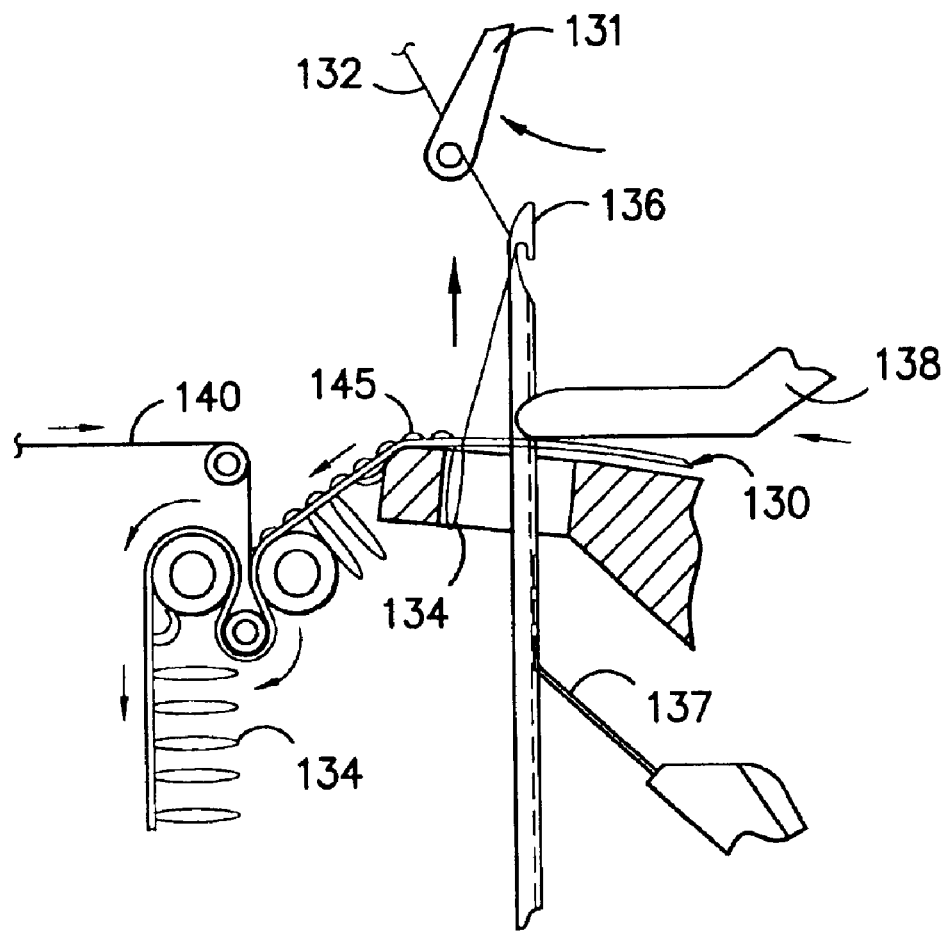
FIG. —4A—

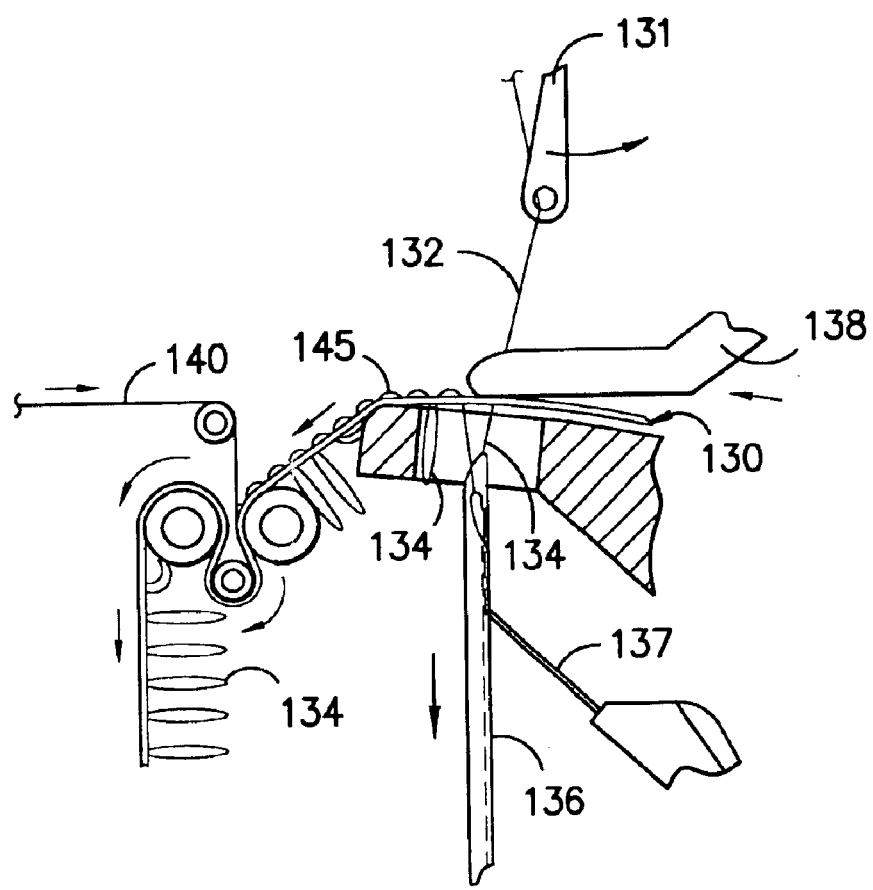
FIG. -4B-

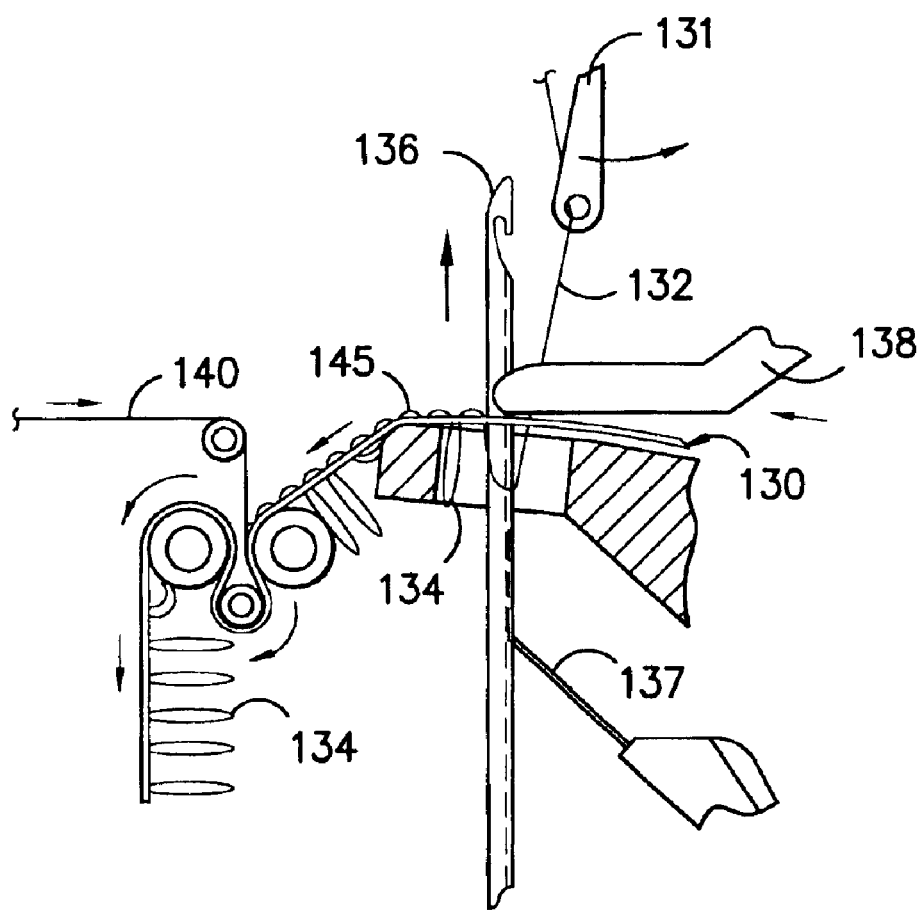
FIG. -4C-

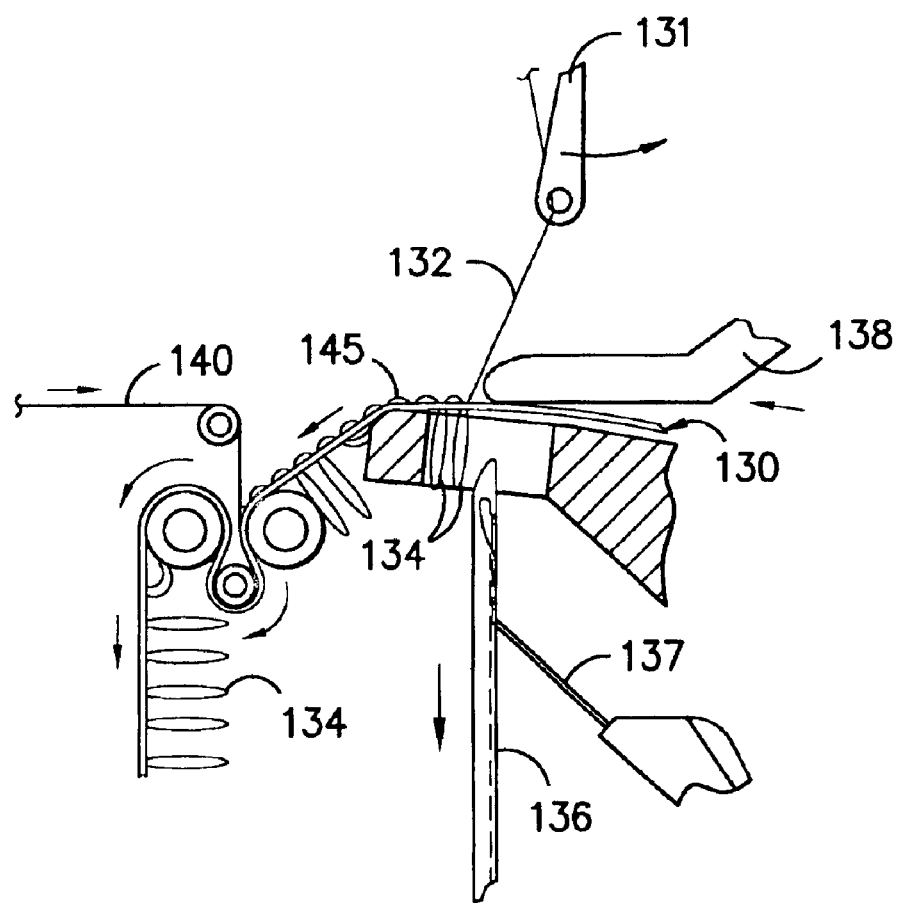
FIG. —4D—

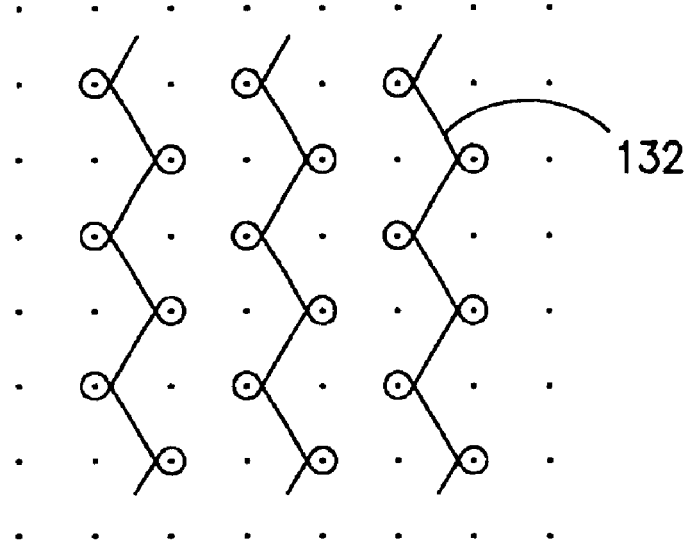
FIG. —5A—
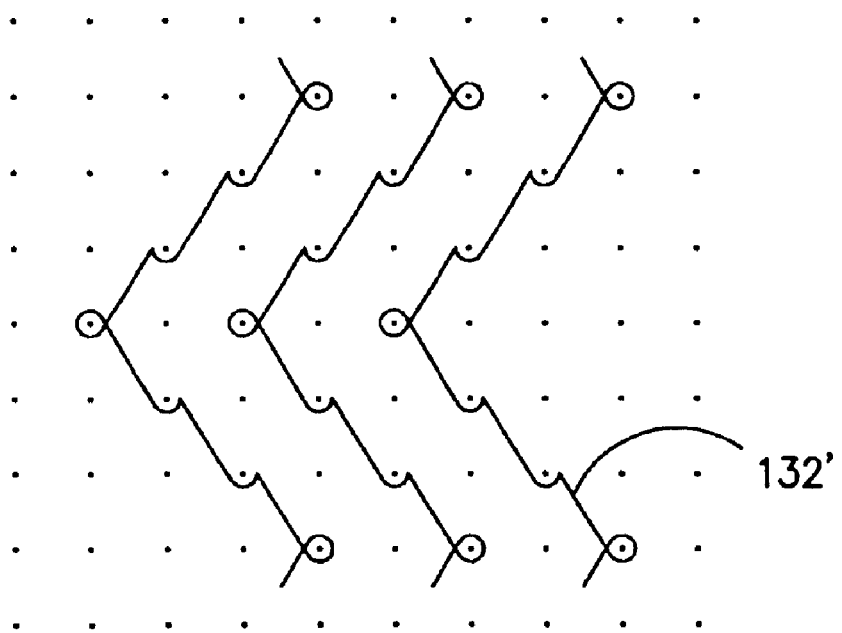
FIG. —5B—

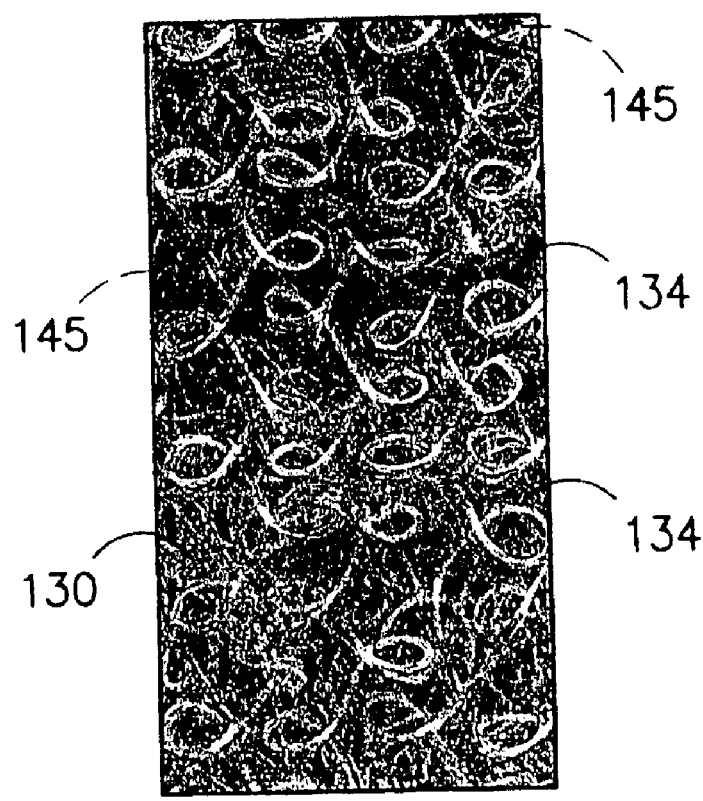
FIG. -6-

FASTENER FABRIC AND RELATED METHOD

TECHNICAL FIELD

The present invention relates to stitch bonded materials and more particularly to stitch bonded materials adapted for use in tear away fastening systems incorporating a loop surface and a cooperating hooking surface.

BACKGROUND OF THE INVENTION

Tear away or contact fastening systems are well known. Such systems incorporate two opposing segments of material which are engageable in substantially juxtaposed relation to one another. A first segment of the material incorporates a plurality of outwardly projecting hooking structures while the second segment of material incorporates a plurality of outwardly projecting loop structures. Upon engagement between the two segments the hooking structures engage the opposing loop structures thereby establishing a bond between the two opposing segments. This bond may be broken by the application of a peel away action between the two opposing segments of material thereby permitting the segments to be progressively disengaged from one another. The engagement may be reactivated by simply bringing the segments back into contacting laminar relation with one another.

In the past, the hooking structures and loop structures across the segments of material have been formed by a variety of practices. According to one practice, a plurality of yarns forming the hooking and/or loop segments have been stitched through a polymeric film in a fully threaded tricot stitch to form loops projecting from a first surface of the film and to form locking portions of the stitches across a second opposite surface of the film. Such a construction is illustrated and described in U.S. Pat. No. 4,931,343 the teachings of which are incorporated by reference as is fully set forth herein. The hook portions which may be either of a classic hook configuration or which have an enlarged head which nonetheless engages the loop portion may be formed by first producing a loop portion of the material and thereafter either cutting the loops along one side to form the hooks or melting the upper portions of the loops to form projections with enlarged heads at their ends.

SUMMARY OF THE INVENTION

The present invention provides advantages and alternatives over the prior art by providing a simplified practice for forming a loop fabric which may be used as part of a tear away fastening system. The practice and resulting loop fabric is not dependent on the formation of locking stitch segments across the side of the structure facing away from the outwardly projecting loops. The quantity of stitching yarn may thereby be substantially reduced while nonetheless maintaining an adequate concentration of loop elements across the surface of the structure. The resulting hook and loop constructions may find uses in any number of attachment applications wherein an easily releasable fastening arrangement is desired. By way of example only, and not limitation, one such environment may be as part of a protective garment such as a diaper or the like to be worn by an infant or adult to control the discharge of bodily waste products.

BRIEF DESCRIPTION OF THE DRAWINGS

The accompanying drawings, which are incorporated in and which constitute a part of this specification illustrate exemplary constructions and procedures in accordance with the present invention and, together with the general description of the invention given above and the detailed description set forth below, serve to explain the principles of the invention wherein:

FIG. 1 illustrates a diaper incorporating a fastening arrangement utilizing cooperating hook and loop structures;

FIG. 2 illustrates schematically a stitch bonding procedure for forming a plurality of loops across one side of an underlying substrate with cooperating interlocking stitches across the other side of the substrate in accordance with prior art practices;

FIG. 3 is an exemplary needle point diagram illustrating a cooperating stitch forming arrangement for forming cooperating loops across a substrate according to the prior art;

FIG. 3A illustrates an arrangement of interlocking stitches across the technical face of the substrate in the stitching arrangement illustrated in FIG. 3 with the loop forming yarn segments across the technical back shown as hidden lines;

FIGS. 4A–4D are views generally similar to FIG. 2 but illustrating steps in a stitch forming practice wherein yarns are pulled through a light-weight substrate to form loop structures across the technical face of the substrate;

FIG. 5A is one exemplary needle point diagram illustrating a pattern utilized to form loops across the technical face of the substrate;

FIG. 5B is one exemplary needle point diagram illustrating a pattern utilized to form loops across the technical face of the substrate; and FIG. 6 is a scanned image of loops across the technical face of a stitch bonded structure formed according to the arrangement illustrated in FIG. 5A.

While the invention has been illustrated and generally described above and will hereinafter be described in connection with certain potentially preferred embodiments and practices, it is to be understood that in no event is the invention limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENT

Turning now to the drawings, in FIG. 1 there is illustrated a diaper 10 including a leg opening 12 and a releasable, adjustable fastening assembly. The fastening assembly incorporates a first segment of material 20 including a plurality of outwardly projecting loop elements 22 and a second segment of material 24 incorporating a plurality of outwardly projecting hooking elements 26. By the term "hooking elements" is meant elements having a geometry adapted to releaseably engage the loop elements 22 upon contact. By way of example only, and not limitation, such hooking elements 26 may be configured to have a hooked terminal end and/or an enlarged terminal end such as a "mushroom" shape or the like to become engaged within the loop elements 22. Of course it is to be appreciated that the relative position of the first segment of material 20 incorporating the loop elements 22 and the second segment of material 24 incorporating the hooking elements 26 may be reversed if desired.

It is to be appreciated that the length of one or both of the first and second segments of material 20, 24 may be adjusted so as to provide a desired arrangement for properly adjusting the diaper 10. By way of example only and not limitation, it is contemplated that in the illustrated arrangement wherein the first segment of material 20 incorporating the loop elements 22 is disposed across a forward portion of the diaper 10 such first segment of material may extend across an extended length thereby providing an extended surface for engagement with the second segment of material 24 during the joining process. This arrangement may facilitate adjustment of the diaper 10 to users of various size.

It is contemplated that the first segment of material 20 and/or the second segment of material 24 may be formed from a material having a plurality of loops disposed across one side. The loops across the material may be used either in loop form to define the loop elements 22 in the first segment of material 20 or may be further treated to form hooks or other hooking elements 26 in the second segment of material 24 in the same manner as disclosed in U.S. Pat. No. 4,931,343.

A method as utilized to form loops 34 in a stitch bonded construction according to the prior art is illustrated in simplified form in FIGS. 2, 3 and 3A. In the prior art practice, a substrate material such as a polymeric film 30 is conveyed to a stitch-forming position. A plurality of stitching yarns 32 are stitched through the substrate 30 to form portions of the stitching yarns 32 into loops 34 projecting from the front face also known as the "technical back" of the substrate 30. As illustrated, the stitching yarns 32 are carried by yarn guides 31 such that the stitching yarns 32 are alternately engaged by reciprocating needles 36 on either side of the sinker bar fingers so as to be passed back and forth in loop-forming fashion over the associated outwardly projecting fingers of a sinker bar 38 thereby forming the loops 34 across the technical back. While for ease of reference only a single needle 36 disposed behind a sinker bar finger is illustrated, it is to be understood that in actual practice a plurality of needles 36 and corresponding stitching yarns are normally disposed across the width of the substrate 30 between spaced sinker bar fingers.

In the prior practice, the needle 36 (which is shown in greatly exaggerated dimension) pierces the substrate 30 and engages the stitching yarn 32 at a position above the sinker bar 38 such that the stitching yarn 32 is captured within a hook portion of the needle 36. As the needle 36 is reciprocated downwardly, a closing element 37 such as a closing wire which moves relative to the needle 36 closes the hook portion to hold the stitching yarn therein. With the hook portion closed, the stitching yarn 32 is pulled through an immediately preceding stitch 33 disposed around the shank of the needle 36 at a position below the substrate 30. As the stitching yarn 32 is pulled through the interior of the preceding stitch 33, the preceding stitch 33 is knocked off of the needle 36 and a new stitch is established by the portion of the stitching yarn held within the hook portion of the needle. As the needle 36 is raised back through the substrate 30 to the position illustrated in FIG. 2, the hook portion is reopened and the new stitch 33 moves out of the hook portion and is held around the shank of the needle 36 for acceptance of a subsequent stitch during the next downstroke.

A needle point diagram illustrating a typical fully threaded loop-forming stitch pattern utilized in the prior art is illustrated in FIG. 3. As will be appreciated by those of skill in the art, this construction utilizes a traditional chain stitch arrangement such that every time the yarn travels around a needle there is a yarn at the preceding needle location. That is, every time a segment of the stitching yarn 32 is pulled through the substrate, that segment engages a loop formed during the preceding stroke. This arrangement gives rise to a pattern of engaging stitches 33 (FIG. 3A) extending in substantially parallel rows in the machine direction across the surface below the substrate 30 (i.e. across the technical face) of the structure. The segments of the stitch yarns forming the loops 34 across the technical back are shown as hidden lines.

As shown, the engaging stitches 33 cooperate with one another in the machine direction of the fabric in a substantially stable interlocking relation thereby anchoring the yarns in place. A break in this sequence results in the loss of this anchoring relation thereby permitting the yarn 32 to be pulled easily out of the substrate 30. As will be appreciated, while the use of the illustrated prior art stitch forming practice produces stable loops 34 across one side of the substrate 30 held in place by the underlying stitches 33 across the opposing side of the substrate 30, such a construction may require a relatively high quantity of stitching yarn 32 to form the stitches 33 across the side of the substrate facing away from the loops 34. This relatively high yarn consumption arises from the fact that a stable anchoring relation between the loops 34 and the stitches 33 is dependent upon a stitch and associated loop being formed at every needle in every cycle in order to avoid a break in the sequence.

The present invention does not rely upon the formation of interlocking stitches to anchor the loops in place. Thus, the prior constraint of forming interlocking stitches and associated loops in a substantially one to one relationship at every needle location is avoided. Loops may thus be formed at lower concentrations per unit area across the substrate. Since stitches are not required to lock the loops in place it may be possible to utilize less yarn and/or lighter weight yarn. In addition, the elimination of the need to form interlocking stitches across the side of the substrate facing away from the loops provides the ability to utilize a wide array of loop forming techniques.

One exemplary practice for forming a loop fabric which may thereafter be used as a segment of a tear away fastening system is illustrated in FIGS. 4A–4D wherein elements corresponding to those previously illustrated and described in relation to FIG. 2 are designated by like reference numerals increased by 100. As illustrated, in this process the stitching yarn 132 does not engage the fingers of the sinker bar 138. Rather the sinker bar 138 is used primarily to hold the substrate 130 in place as the stitching yarn is periodically pulled through the substrate 130 so as to form a plurality of loop elements 134 across the back side or so-called "technical face" of the substrate 130.

In the illustrated practice, a substrate 130 is conveyed under tension to a stitch-forming position at which a reciprocating needle 136 moves through the substrate. During formation, a plurality of stitching yarns carried by dynamic yarn guides 131 are engaged by reciprocating needles at a position above the substrate 130 in the manner as previously described. While for ease of reference only a single needle 136 disposed behind a sinker bar finger is illustrated, it is to be understood that in actual practice a plurality of needles 136 and corresponding stitching yarns 132 are normally disposed across the width of the substrate 130 (i.e. in the cross machine direction) between spaced sinker bar fingers.

In the illustrated practice which makes use of traditional stitch bonding equipment, the needle 136 (which is shown in greatly exaggerated dimension) pierces the substrate 130 and engages the stitching yarn 132 supported by a moveable yarn guide 131 at a position above the substrate 130 such that the stitching yarn 132 is captured within a hook portion of the needle 136 (FIG. 4A). As the needle 136 is reciprocated downwardly, a closing element 137 such as a closing wire which moves relative to the needle 136 closes the hook portion to hold the stitching yarn therein as it is pulled through the substrate 130. Contrary to the prior art practice, no immediately preceding stitch is disposed around the shank of the needle 136 below the substrate 130. Thus, as the stitching yarn 132 is pulled through the substrate 130 and away from the underside of the substrate 130, a loop 134 is formed across the technical face (FIG. 4B).

After formation of the loop. 134, the needle 136 is raised and the hook portion is reopened thereby permitting the loop 134 formed on the downstroke to slide out of the hook portion and around the shank of the needle 136 (FIG. 4C). On the next downstroke, the yarn guide 134 is shifted away from the needle path such that the stitching yarn 132 does not engage the needle 136. As the needle 136 travels downwardly, the previously formed loop 134 is knocked off of the needle 136 (FIG. 4D). A series of discrete loops 134 is thus formed across the technical face with intermediate yarn segments 145 extending between the loops 134 across the technical back.

As will be appreciated, during the downstroke of the needle 136 when the stitching yarn 132 is not engaged, it is contemplated that the stitching yarn 132 may either remain disengaged from any needle or may engage an adjacent needle (not shown). In the event that an adjacent needle is engaged, the stitching yarn 132 is pulled through the substrate 130 and forms a loop in adjacent diagonal relation to the first formed loop. Of course it is to be understood that any number of arrangements for the engagement and disengagement of the stitching yarn 132 by needles may be used to form a desired concentration and pattern of loops 134 across one side of the substrate 130 with intermediate yarn segments 145 disposed across an opposing side of the substrate 130.

By way of example only, in FIG. 5A a needle point diagram is provided illustrating a half threaded tricot stitch arrangement as may be used in the present invention. As will be appreciated by those of skill in the art, in this arrangement loops are formed at every other needle point along needle lines with the stitching yarn 132 shifting back and forth between adjacent needle lines. Another contemplated arrangement is illustrated in FIG. 5B. In this arrangement the stitching yarns 132' form loops at needle points disposed along multiple lines before shifting back to the starting needle line. It is also contemplated that the stitching yarns need not shift between needle lines in which case the stitching yarns will be arranged in a straight stitch configuration having a form corresponding generally to a sine wave. By using any of these arrangements a stitch bonded construction may be formed in which the yarn intentionally skips engagement with the needle in a needle line according to a predefined sequence thereby avoiding the formation of a substantially continuous stitch pattern along the needle line. Of course, loop forming arrangements other than those illustrated may likewise be utilized if desired. Generally, it is contemplated that any number of partially threaded stitch patterns may be utilized where engagement between the yarn 132 and the needle 136 is skipped at one or more needle points between loops along each needle line.

As will be appreciated by those of skill in the art, the failure of the yarn 132 to engage the needle 136 at each needle point along the needle line gives rise to a so-called "drop stitch" phenomenon. Such a drop stitch would normally be considered to be a defect in a stitch-bonded product due to the fact that the loop formed lacks an anchoring relation across the side of the substrate facing away from the loop. That is, the intermediate yarn segments 145 extending across the technical back are stitched into a cooperating structure across the technical back. The intermediate yarn segments 145 can thus be pulled freely away from the technical back which in turn permits the associated opposing loops 134 to be pulled out of the technical face. However, in the present invention the occurrence of a drop stitch is utilized intentionally to substantially reduce the overall quantity of yarn disposed across the side of the substrate facing away from the loops 134 and thereby reducing the overall quantity of stitching yarn 132 required.

Due to the fact that the stitching yarn 132 is not anchored in place within the substrate 130, it is contemplated that a backing 140 such as a preformed polymeric adhesive film, thermoplastic coating, heat cureable dispersion or the like may be applied across the technical back of the material as it is formed. Of course, it is contemplated that other stabilizing materials may be utilized if desired. By way of example only, according to one contemplated practice, the backing 140 may be a thermoplastic coating applied by a continuous slot die or extrusion coater as will be well known to those of skill in the art. As will be appreciated, in such a construction the backing is melt bonded in affixed relation to the substrate. According to another contemplated practice, the backing 140 may be an aqueous dispersion such as SBR latex applied by a spraying or roll coating process. As previously indicated, the substrate 130 may be of a generally low strength material. Thus, the backing may serve the dual roles of providing strength to the overall composite as well as anchoring the yarn in place across the technical back.

In FIG. 6, a scanned image is provided illustrating an exemplary stitch bonded structure formed according to the needle point diagram illustrated in FIG. 5A with loops 134 formed across the technical face of an underlying nonwoven substrate 130. As will be appreciated, the loops 134 are formed at alternating needle points where the needle 136 has engaged the yarn 132 and pulled it through the substrate 130. Thus, the loops 134 are arranged in substantially parallel rows extending in the machine direction of the formed composite. Intermediate yarn segments 145 extend between the loops 134 across the underside of the nonwoven substrate. As can be seen, the intermediate yarn segments 145 are visible through the substrate 130 due to the light construction of the substrate 130.

While it is contemplated that stitch bonding practices may be used to efficiently form loops 134 across one side of a substrate 130, it is likewise contemplated that any number of other manual or automated formation techniques may also be utilized. By way of example only, it is contemplated that a yarn may be tufted through the substrate to form a looped pile across one side using standard tufting practices as will be known to those of skill in the art. It is also contemplated that a yarn may be pushed or pulled manually through the substrate. If desired, it is also contemplated that the loop forming yarn in any of the constructions may include a thermoplastic constituent to facilitate heat activated bonding to the substrate so as to improve positional stability.

It has been found that loop forming constructions according to the present invention afford the ability to substantially reduce the overall requirement for stitching yarn required due to the fact that cooperating stitches and loops are not required to be formed at each needle point. While a backing 140 is used to promote the positional stability of the intermediate yarn segments 145, across the side of the substrate facing away from the loops 134, it has been found that the presence of the backing may afford the benefit of permitting a very lightweight substrate 130 to be utilized. The ability to use such a substrate material arises from the fact that the substrate 130 is no longer required to provide substantial structural stability since the backing provides such stability. By way of example only and not limitation, contemplated substrate materials may include light weight fibrous webs of needle punched, hydroentangled, or spun bonded fibers with relatively low levels of coherency between the fibers. Light weight films may also be utilized. Very light weight gossamer-like spun bonded polyester or polypropylene having a mass per unit area of about 15 grams per square meter may be particularly preferred.

Due to the fact that the yarns 132 are not required to provide substantial structural integrity to the system of the present invention, it is contemplated that the present invention may afford additional flexibility in the selection of yarn types for use in the formation of the loops. In this regard it is contemplated that virtually any yarn type as may be desired may be utilized. By way of example only, contemplated yarn materials include polyester, polypropylene and nylon. Such yarns may be either multi-filament or mono-filament in construction. Moreover, a wide range of linear densities may be utilized in the yarns. By way of example only, and not limitation it is contemplated that the yarns 132 used to form the loops 134 may have a linear density in the range of about 40 denier although if stronger loops are desired the denier may be increased up to about 1000 denier or more.

It is to be understood that while the present invention has been illustrated and described in relation to certain potentially preferred embodiments, constructions and procedures, that such embodiments, constructions and procedures are illustrative only and that the present invention is in no event to be limited thereto. Rather, it is contemplated that modifications and variations embodying the principles of this invention will no doubt occur to those of to those of skill in the art in the art. It is therefore contemplated and intended that the present invention shall extend to all such modifications and variations as may incorporate the broad aspects of the invention within the full spirit and scope thereof.

What is claimed is:

1. A multi-layer sheet material adapted to be used as a portion of a tear away fastening system, said sheet material comprising:
   a substrate layer;
   and a plurality of loop forming yarns extending through said substrate layer such that said loop forming yarns define a plurality of loop elements projecting away from said substrate layer and wherein said loop elements are interconnected by portions of said loop forming yarns defining intermediate yarn segments disposed across a face of said substrate layer projecting away from said loop elements, wherein the intermediate yarn segments are substantially free of interlocking relation to other yarn segments disposed across said face of said substrate layer projecting away from said loop elements and wherein said loop elements are arranged in a discontinuous pattern along substantially parallel rows of needle punctures such that the loop forming yarns extend across the substrate layer through a first portion of said needle punctures and such that a second portion of said needle punctures devoid of loop forming yarns is disposed in a predefined pattern to occupy positions between at least a portion of said loop elements along said parallel rows of needle punctures whereby the number of said loop elements is less than the total number of needle punctures along said parallel rows of needle punctures; and
   a backing layer disposed in substantially fixed relation to said face of said substrate layer projecting away from said loop elements to hold the intermediate yarn segments in place.

2. The invention as recited in claim 1, wherein said plurality of loop forming yarns are stitched through said substrate in a partially threaded tricot stitch arrangement.

3. The invention as recited in claim 1, wherein said loop forming yarns extending through said substrate are characterized by a linear density in the range of about 40 denier to about 1000 denier.

4. The invention as recited in claim 3, wherein said loop forming yarns are multi-filament yarns.

5. The invention as recited in claim 4, wherein said multi-filament yarns comprise synthetic materials selected from the group consisting of polyester, polypropylene, and nylon.

6. The invention as recited in claim 3, wherein said loop forming yarns are mono-filament yarns.

7. The invention as recited in claim 6, wherein said mono-filament yarns comprise synthetic materials selected from the group consisting of polyester, polypropylene, and nylon.

8. The invention as recited in claim 1, wherein said substrate layer comprises a web of entangled synthetic fiber elements.

9. The invention as recited in claim 8, wherein said web of entangled synthetic fiber elements is of a spun bonded construction.

10. The invention as recited in claim 8, wherein said web of entangled synthetic fiber elements is characterized by a mass per unit area in the range of about 15 grams per square meter.

11. The invention as recited in claim 1, wherein said substrate layer comprises a film.

12. The invention according to claim 1, wherein said backing layer comprises an adhesive film.

13. The invention according to claim 1, wherein the backing layer comprises a thermoplastic coating melt bonded to said face of said substrate layer projecting away from said loop elements.

14. A multi-layer sheet material adapted to be used as a portion of a tear away fastening system, said sheet material comprising:
a stitch bonded composite and a backing layer, wherein said stitch bonded composite comprises a substrate layer of entangled fiber elements and a plurality of loop, forming yarns extending in a repeating stitch pattern through said substrate layer at locations along the length of said substrate layer such that said yarns define a plurality of loop elements projecting away from a first face of said substrate layer in substantially parallel rows extending along the length of said substrate layer and wherein loop elements within said substantially parallel rows are interconnected by portions of said loop forming yarns defining intermediate yarn segments disposed in crossing relation between at least a portion of said substantially parallel rows across a second face of said substrate layer projecting away from said first face, wherein said repeating stitch pattern is a partially threaded stitch pattern comprising a predefined pattern of dropped stitches disposed along said substantially parallel rows and wherein said backing layer is disposed in substantially fixed relation to said second face of said substrate layer to hold the intermediate yarn segments in place across said second face of said substrate layer.

15. The invention as recited in claim 14, wherein said substrate layer of entangled fiber elements is of a spun bonded construction.

16. The invention as recited in claim 14, wherein said substrate layer of entangled fiber elements is of a spun bonded construction characterized by a mass per unit area in the range of about 15 grams per square meter.

17. The invention as recited in claim 14, wherein said loop forming yarns are multi-filament yarns.

18. The invention as recited in claim 14, wherein said loop forming yarns are mono-filament yarns.

19. In a diaper, a tear away fastening system comprising at least two segments of cooperatively engageable material wherein at least one of the segments of material comprises a substrate layer of entangled fiber elements; a plurality of loop forming yarns extending through said substrate layer such that said loop forming yarns define a plurality of loop elements projecting away from said substrate layer wherein said loop elements are arranged in a discontinuous pattern along substantially parallel rows of needle punctures through said substrate layer such that the loop forming yarns extend through the substrate layer through a first portion of said needle punctures and such that a second portion of said needle punctures devoid of loop forming yarns is disposed in a predefined pattern to occupy positions between at least a portion of said loop elements along said parallel rows of needle punctures, whereby the number of said loop elements is less than the total number of needle punctures along said parallel rows of needle punctures, and wherein said loop elements are interconnected by portions of said yarns defining intermediate yarn segments disposed in crossing relation between at least a portion of said substantially parallel rows of needle punctures across a face of said substrate layer projecting away from said loop elements, wherein the intermediate yarn segments are substantially free of interlocking relation to other yarn segments disposed across said face of said substrate layer projecting away from said loop elements; and wherein a backing layer is disposed in substantially fixed relation across said face of said substrate layer projecting away from said loop elements to anchor the loop elements in place.

20. The invention as recited in claim 19, wherein said substrate layer of entangled fiber elements is of a spun bonded construction characterized by a mass per unit area in the range of about 15 grams per square meter.

21. The invention as recited in claim 19, wherein said loop forming yarns are multi-filament yarns.

22. The invention as recited in claim 19, wherein said loop forming yarns are mono-filament yarns.

* * * * *